(12) United States Patent
Liang et al.

(10) Patent No.: US 7,238,348 B2
(45) Date of Patent: Jul. 3, 2007

(54) METHOD OF TREATMENT OF OSTEOPOROSIS WITH COMPOSITIONS OF RED RICE FERMENTATION PRODUCTS

(75) Inventors: Zhang Mao Liang, Beijing (CN); Duan Zhen Wen, Beijing (CN); Peng Chi Xiu, Beijing (CN); Zhou Yu-Fang, Beijing (CN); Guo Shuren, Beijing (CN); He Dalin, Beijing (CN)

(73) Assignee: Beijing Peking University WBL Corporation Ltd., Beijing (CN)

( * ) Notice: Subject to any disclaimer, the term of this patent is extended or adjusted under 35 U.S.C. 154(b) by 486 days.

(21) Appl. No.: 10/354,537

(22) Filed: Jan. 28, 2003

(65) Prior Publication Data

US 2003/0157068 A1 Aug. 21, 2003

Related U.S. Application Data

(60) Continuation-in-part of application No. 09/542,438, filed on Apr. 4, 2000, now Pat. No. 6,632,428, which is a division of application No. 08/965,202, filed on Nov. 6, 1997, now Pat. No. 6,046,022, which is a continuation-in-part of application No. 08/720,548, filed on Sep. 30, 1996, now abandoned.

(51) Int. Cl.
*A61K 35/70* (2006.01)
*C12N 1/14* (2006.01)
(52) U.S. Cl. .................................. 424/93.5; 435/254.1
(58) Field of Classification Search ............... 424/93.5; 435/254.1
See application file for complete search history.

(56) References Cited

U.S. PATENT DOCUMENTS

| | | | |
|---|---|---|---|
| 3,983,140 A | 9/1976 | Endo et al. ............... | 260/343.5 |
| 4,031,250 A | 6/1977 | Haas et al. .................... | 426/18 |
| 4,049,495 A | 9/1977 | Endo et al. .................... | 195/36 |
| 4,137,322 A | 1/1979 | Endo et al. .................. | 424/273 |
| 4,231,938 A | 11/1980 | Monaghan et al. ...... | 260/343.5 |
| 4,294,846 A | 10/1981 | Albers-Schonberg et al. ......................... | 424/279 |
| 4,294,926 A | 10/1981 | Monaghan et al. ......... | 435/125 |
| 4,319,039 A | 3/1982 | Albers-Schonberg et al. ......................... | 560/256 |
| 4,342,767 A | 8/1982 | Albers-Schonberg et al. ......................... | 424/250 |
| 4,420,491 A | 12/1983 | Albers-Schonberg et al. ......................... | 424/311 |
| 5,362,638 A | 11/1994 | Dahiya ....................... | 435/125 |
| 5,627,068 A | 5/1997 | Kujumdzieva et al. .. | 435/254.1 |
| 5,712,130 A | 1/1998 | Hajko et al. ............... | 435/123 |
| 6,046,022 A * | 4/2000 | Zhang et al. ................ | 435/41 |
| 6,410,521 B1 * | 6/2002 | Mundy et al. .............. | 514/100 |
| 2006/0078533 A1* | 4/2006 | Omoigui ................... | 424/78.14 |

FOREIGN PATENT DOCUMENTS

| | | |
|---|---|---|
| CN | 1075875 A | 9/1993 |
| CN | 1106230 A | 8/1995 |
| CN | 1110560 A | 10/1995 |
| CN | 1155421 A | 7/1997 |
| CN | 1173361 A | 2/1998 |
| DE | 3006216 | 2/1980 |
| DE | 3051175 | 2/1980 |
| GB | 2046737 | 2/1980 |
| GB | 2055100 | 7/1980 |
| JP | 55-150898 | 11/1980 |
| JP | 58-43783 A | 3/1983 |
| JP | 62-132878 A | 6/1987 |
| JP | 63-198973 A | 8/1988 |
| WO | WO-99/23966 * | 5/1999 |

OTHER PUBLICATIONS

Wang et al. (English Abstract). Oct. 1995., Journal of the Formosan Medical Association=Taiwan yi zhi, vol. 94, No. 10, pp. 589-592.*
Demain, et al., Manual of Industrial Microbiology and Biotechnology, American Society for Microbiology, 1986, pp. 66-83 and 87.*
Yan, Z., et al. (1999) Effects of xuezhikang on blood lipids and lipoprotein concentrations of rabbits and quails with hyperlipideaemia. Chinese Pharmaceutical Journal, 30(11):656-660.
Han, M., et al. (1994) Experimental study on the decholesterolization of metabolites from monascus rubber. Microbiology, 21(5):279-280.
Read, B.E. and Liu, J.C. (1927), Chinese Medicinal Plants from the Pen Ts'ao Kang Mu, 3rd edition, published by Peking National History Bulletin.
T'ien-Kung K'ai-Wu chinese technology in the seventeenth century, translated by E-tu Zen Sun and Shiou-Chuan Sun, The Pennsylvania State University Press pp. 291-294, 1966.
Fielding, B.C., et al. (1961), The chemistry of fungi. part XXXIX. The structure of monascin. J. Chem. Soc. 4579-4589.
Broder, C.U. and Koehler, P.E. (1980) Pigments produced by monascus purpureus with regard to quality and quantity. J. Food Sci. 45:567-469.
Wong H. and Bau, Y. (1977) Pigmentation and antibacterial activity of fast neutron- and x-ray- induced strains of monascus purpureus went. Plant Physiol, 60:578-581.
Feling, P. and Wahren, J. (1975) Fuel homeostasis in exercise. N. Eng. J. Med. 293:1078-1084.
Grundy, S.M. (1988) HMG-CoA reductase inhibitors for treatment of hypercholesterolemia. New Eng. J. Med. 319:24-33.
Endo, A., (1976) New inhibitors of cholesterogenesis produced by penicillium citrinum. J. Antibiotics, 29:1346-1348.
Tsujita, Y., et al. (1979) Hypolipidemic effects in dogs of ML-236B, a competitive inhibitor of 3-hydroxy-3-methylglutaryl coenzyme a reductase. Atherosclerosis 32:307-313.

(Continued)

*Primary Examiner*—Ralph Gitomer
*Assistant Examiner*—Kailash C. Srivastava
(74) *Attorney, Agent, or Firm*—Fish & Richardson P.C.

(57) ABSTRACT

Methods are disclosed for using red rice fermentation products for the treatment or prevention of osteoporosis and abnormal bone mass conditions. Particular *Monascus* strains yield fermentation products with the desired biological activities.

3 Claims, No Drawings

OTHER PUBLICATIONS

Endo, A. (1979) Monacolin K, a new hypo-Cholesterlemic agent produced by a monascus species. J. Antibiotics 32:852-854.

Endo, A. (1980) Monacolin K, a new hypto-cholesterolemic agent the specifically inhibits 3-hydroxy-3-methylglutaryl coenzyme a reductase. J. Antibiotics 33:334-336.

Tobert, J.A., et al. (1982) Cholesterol-lowering effect of mevinolin, an inhibitor of 3-hydroxy-3-methylglutaryl-coenzyme a reductase, in healthy volunteers. J. Clin Invest. 69:913-919.

Tobert, J.A. (1988) Effecacy and long-term adverse effect of lovastatin. Am J. Cardiol. 62:28J-34J.

The Merck Manual of Diagnosis and Therapty (1992) 16th edition, pp. 1044-1046.

Pi-Sunyer, F.X. (1991) Health implications of obesity. Am J. Clin Nutr. 53:1595S-1603S.

* cited by examiner

METHOD OF TREATMENT OF OSTEOPOROSIS WITH COMPOSITIONS OF RED RICE FERMENTATION PRODUCTS

CROSS-REFERENCE TO RELATED APPLICATIONS

This application is a continuation in part of U.S. patent application Ser. No. 09/542,438, filed 4 Apr. 2000, now U.S. Pat. No. 6,632,428, which is a divisional of Ser. No. 08/965,202, filed 6 Nov. 1997, now U.S. Pat. No. 6,046,022, which is a continuation-in-part of Ser. No. 08/720,548, filed 30 Sep. 1996, now abandoned, all of which are incorporated herein by reference in full.

FIELD OF THE INVENTION

The invention relates to the fields of rice fermentation and treatment of osteoporosis. More particularly, the invention relates to red rice fermentation products and use of the products to treat osteoporosis.

BACKGROUND OF THE INVENTION

The invention relates to compositions comprising red rice fermentation product, that can be used to treat osteoporosis and related abnormal bone mass conditions in mammals, including humans.

Red Rice in Ancient China

Red rice is known mostly for its use in food as a preservative and colorant and its uses in the dye industry. Red rice (known in Chinese as Hung-ch'u or Hongqu) has also been known and used for hundreds of years in China in rice wine making and as a food preservative. In addition, red rice has been known as an ancient Chinese medicine or an ingredient in certain ancient Chinese prescriptions.

Red rice was first used around the time of the Han Dynasty. Tao Gu, who lived in the age of Wudai after the Tang Dynasty, recorded "Red Yeast Rice Cooked with Meat," in *Qing Yi Lu*. The method of making red rice was originally recorded in *T'ien Kyng K'ai Wu* and *Pen Ts'ao Kang Mu*. A detailed description of the medical applications of red rice was provided in the ancient Chinese pharmacopoeia, *Pen Ts'ao Kang Mu*, which was published during the Ming Dynasty (1368-1644). In *Pen Ts'ao Kang Mu*, red rice is described as mild, nonpoisonous, and useful for treating indigestion and diarrhea. Red rice is also described as useful for improving blood circulation and promoting the health of the spleen and stomach. Furthermore, several "prescriptions" using red rice for treating ailments, such as indigestion, diarrhea, and heart and abdominal pains, are also provided in this ancient work. In accordance with the Traditional Chinese Medicine Standard set forth in *Pharmacopoeia of People's Republic of China* and the Traditional Chinese Medicine standard of Beijing, Nei Monggol, Shandong Province, Jiangsu Province and Hunan Province, etc., red rice is specified to be used as a traditional Chinese medicine. Furthermore, in the textbooks of Chinese universities and colleges such as *Food Additives* and *Food Chemistry*, red rice is considered an additive for food and beverages, and has been widely used in the food processing industry for the production of such items as fermented bean curd, beer, and meat.

In an abbreviated English, translation of *Pen Ts'ao Kang Mu* published in 1911, red rice is described as useful for fermentation and having medicinal value in the treatment of postpartum difficulties in women and dyspeptic conditions in children (Stuart, M. D., in *Chinese Materia Medica—Vegetable Kingdom*, pages 233-234, republished in 1979 by Southern Materials Center, Inc., Taipei, Republic of China). Red rice, as described in *Pen Ts'ao Kang Mu*, was subsequently recognized to be the fungal species known as *Monascus purpureus* Went (Read, B. E., 1936, Chinese Medicinal Plants from the *Pen Ts'ao Kang Mu*, 3rd edition, published by Peking National History Bulletin; Klein, G., 1932, Handbuch der Pflanzenanalyse II, p. 1422-1423, Wien, Verlag von Julius Springer).

The manufacture of red rice is taught in another publication from the Ming Dynasty, *Tien Kung K'ai Wu* by Sung Ying-Hsing, which was published in 1637 A. D. (see pages 291-294 in the English translation of this ancient writing, *T'ien Kung K'ai Wu—Chinese Technology in the Seventeenth Century*, translated by E-tu Zen Sun and Shiou-Chuan Sun, the Pennsylvania State University Press 1966). Red rice is described therein as useful for preserving the color and taste of fish or meat. The manufacturing process used red wine mash and cooked nonglutinous rice as starting materials. The method of making red rice by allowing the fungus to grow on the surface of cooked rice was also recorded by Voderman (1894, Analecta ob Cromatologisch Gebied. II. Geneesh. Fylschrift voor Ned. Indie, 35, No. 5).

Red rice, the fermentation product of *Monascus* species, is still used in traditional Chinese medicine, wine making and food coloring in Asia and Asian communities in North America. The red and yellow pigments of *Monascus purpureus*, such as monascorubin and monascin, have been purified and extensively studied (Fielding et al., 1961, *J Chem Soc*, 4579-4589). The culture conditions and effect on pigmentation of *Monascus purpureus* have also been studied (Broder et al., 1980, *J Food Sci*, 45:567-469). Antibacterial activity, especially against *Bacillus* species, was also detected in *Monascus purpureus* extract (Wong, 1977, *Plant Physiol*, 60:578-581). The red rice of the traditional methods has been shown to be of little value and thus has gradually fallen out of use in medical applications.

Osteoporosis is a systemic skeletal disease characterized by low bone mass and deterioration of bone tissue. The effect is the increase in bone fragility and susceptibility to fracture. There are two categories of osteoporosis: primary osteoporosis and secondary osteoporosis. Type I primary osteoporosis, post-menopausal osteoporosis, is characterized by disproportionate loss of trabecular bone. Type II primary osteoporosis is age-associated and affects all skeletal sites, with both cortical and cancellous bone. Type III primary osteoporosis is idiopathic osteoporosis, which affects pre-menopausal women as well as middle-aged and young men.

Secondary osteoporosis is caused by an identifiable agent such as glucocorticoids or by a disease such as hyperthyroidism or myeloma. The most common cause of osteoporosis is estrogen deficiency in post-menopausal women. The major health consequence of osteoporosis is osteoporotic fracture, which may occur at any skeletal site, but the primary sites are the spine, hip and distal forearm. With respect to the definition of persons in need of treatment, a normal person is defined as having a bone mass density (BMD) within one standard deviation (SD) of the young adult mean. A person with the condition of osteopenia is a person having a BMD value of more than one SD, but less than 2.5 SD below the young adult mean. A person with osteoporosis is typically defined as having a BMD value of 2.5 SD or more below the young adult mean.

Historically, the most effective approach to treatment of osteoporosis is through prevention, which is done by optimizing peak bone mass at skeletal maturity, by preventing bone loss or by restoring the bone mineral and architecture in osteoporotic bones. Although peak bone mass is primarily controlled by genetic factors, while growing, the amount of bone tissue that is deposited within the skeleton may be modified by diet, lifestyle or the presence of chronic disease. Bone mass at skeletal maturity can be optimized by intake of calcium, protein, carbohydrates, fat and other nutrients. Exercise and abstinence from tobacco, alcohol and drugs are also beneficial for the skeleton.

Calcium has been shown to be a significant factor for creating optimum bone mass. Increase in calcium intake for post-menopausal women, not yet showing any signs of osteopenia or osteoporosis, is an accepted preventative protocol. Adequate vitamin D is also believed to be helpful since the metabolites of vitamin D are important in the regulation of calcium metabolism. Although vitamin D is found in abundant amounts in fish liver oils and in smaller amounts in oily saltwater fish, egg, butter, margarine and milk, often a daily vitamin D supplement is also necessary to reach the intake level that will prevent vitamin D deficiency.

Once there is onset of osteoporosis, restoration of the skeleton is difficult. Therapeutic options include administration of estrogens in post-menopausal women and administration of bisphosphonates. Varied results have been shown using treatment with vitamin D or its analogs and administration of fluoride.

Accordingly, the choice of protocols for prevention and treatment of osteopenia and osteoporosis is limited. It is therefore desirable to develop more options and more advantageous methods for treating these conditions.

SUMMARY OF THE INVENTION

The invention relates to a product of the fermentation of at least one Monascus strain that can be used as a therapeutic medicament to treat or prevent osteoporosis in humans. The invention is based, in part, on the surprising discovery that certain red rice products, i.e., the product of the fermentation of certain strains or mixtures of strains of Monascus, are effective in mammals, particularly humans.

In various embodiments of the invention, red rice can be used as a medicament to treat or prevent osteoporosis, osteopenia and associated abnormal bone mass conditions. The present invention encompasses methods for treating or preventing these conditions in a human, which comprise administering to the human a therapeutically effective amount of a red rice fermentation product.

Red rice can be manufactured in various dosage forms and formulations. Also disclosed are methods for manufacturing red rice which are based on the traditional fermentation procedures.

The terms "red rice fungi" or "*Monascus*" as used herein refer to the prefermented organism, while the terms "red rice," "red rice product", "red rice extract" and the like refer to a product that results from the fermentation of at least one *Monascus*. Further, these latter terms include traditional and improved red rice products as described below. More specifically, "red rice product" as used herein refers to the product of fermentation, e.g., the fermentate of one or a mixture of *Monascus* fungus. A "lovastatin-producing" *Monascus* strain (such as strain 0272) is one which can be fermented to produce a product having a lovastatin content of at least 0.05%, preferably at least 2%.

The red rice product is the fermentation product of at least one of the following Monascus fungi set forth in the table below.

Red rice is the fermentation product of one or a mixture of *Monascus* fungi, comprising chiefly *Monascus purpureus* Went, and in lesser proportions other *Monascus* species, e.g., *Monascus ruber* van Tieghem, *Monascus Fuliginosus* Sato, *Monascus Pilosus* Sato and *Monascus albidus* Sato. Red rice can also be the fermentation product of the following strains of *Monascus fungi*:

| Strains | Accession No. |
| --- | --- |
| Monascus albidus Sato | AS 3.570 |
|  | AS 3.4440 |
|  | CGMCC No. 0317 |
| Monasuc pilosus Sato | AS 3.4444 |
|  | AS 3.4633 |
|  | AS 3.4646 |
|  | AS 3.4647 |
| Monascus pubigerus Sato | AS 3.4445 |
| Monascus ruber van Tieghem | AS 3.549 |
|  | CGMCC No. 0315 |
|  | CGMCC No. 0316 |
| Monascus paxii Lingelsheim | AS 3.4453 |
| Monascus fuliginosus Sato | AS 3.569 |
|  | AS 3.1098 |
|  | AS 3.2091 |
|  | AS 3.2093 |
|  | AS 3.2134 |
|  | IFFI 05035 |
| Monascus purpureus Went | CGMCC No. 0272 |

Monascus purpureus Went ATCC 30141, AS 3.562, AS 3.991, AS 3.4446 [ATCC 16365], AS 3.4642 [NRRL 2897], AS 3.4643 [NRRL 96], AS 3.4644, AS 3.4645, AS 3.4651; Monascus ruber van Tieghem AS 3.549, IFFI 05007, IFFI 05008, IFFI 05010, IPPI 05011; and Monascus anka IFFI 05038 (reference numbers provided in *China Catalogue of Cultures,* 1992, China Committee for Culture Collection of Microorganism, China Machine Press, Beijing 1992). The improved red rice of the invention comprises Monascus purpureus Went mutant strain M4027, 4028 and M4184.

The term "traditional red rice" as used herein refers to a red rice product which is the result of fermentation using a mixture of *Monascus* fungi that has been used traditionally to manufacture red rice. "Traditional red rice" will generally contain less than about 0.005% lovastatin by weight. According to the invention, an "improved red rice" is produced by fermentation using one or more natural or mutant strains of *Monascus* species, which yield a fermentate with improved biological or nutritional properties, e.g., improvement of conditions which otherwise lead to osteoporosis. An improved red rice of the invention comprises *Monascus purpureus* Went mutant strain CGMCC No. 0272. Several other strains can be used to achieve the objectives of the invention. Improved red rice is sometimes referred to herein as Xuezhikang.

Generally, the red rice products of the present invention are red-purple powders that have a slightly bitter but mild and pleasant taste. Similarly, the red rice products have a pleasant odor. The color and/or odor may vary with the fermentation process, the strains used and the processing steps. The red rice products of the invention contain at least 0.05% lovastatin, more preferably at least about 2.0% lovastatin by weight.

As used herein, the term "effective treatment" means the reduction of a particular symptom or the significant change of a particular laboratory test result toward the normal value. Preferably symptoms are relieved by at least 30-70%, and a laboratory test result is changed at least 10% toward the normal value; more preferably symptoms are reduced by 70% and/or a laboratory test result is changed at least 20% toward the normal value; most preferably, a treatment is effective if the symptoms are reduced by 90%, and/or laboratory parameters are returned to the normal value.

As discussed above, persons exhibiting normal bone mass density exhibit a BMD value within 1 SD of the young adult mean. Osteopenia is indicated by a variation in BMD of more than 1 SD, but less than 2.5 SD below the young adult mean. Osteoporosis is typically defined by a BMD value of 2.5 SD or more below the young adult mean. Most densitometry reports provide SD's from the normal young adult mean in the form of T scores. Some densitometry reports also report Z scores, which represent the SD's from age and sex-matched controlled subjects. The Z score can provide useful diagnostic information because a Z score of two or more below the age and sex-matched control may suggest a secondary cause of osteoporosis. For each 10% decrease in bone mass density, the fracture risk approximately doubles. The BMD measurement at any axial (that is, hip, vertebrae) or peripheral (that is, radius calcaneus) site is useful for a one-time assessment of fracture risk.

The term "therapeutically effective amount" or "therapeutic dose" as used herein means the amount of a particular agent sufficient to provide a therapeutic benefit in the treatment or prevention of a disease.

The term "dietary supplement" as used herein means an additional element that is added to the daily food intake of a mammal, usually a human.

Unless otherwise defined, all technical and scientific terms used herein have the same meaning as commonly understood by one of ordinary skill in the art to which this invention belongs. Although methods and material similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DETAILED DESCRIPTION OF THE INVENTION

The invention relates to a method of use of compositions comprising the product of the fermentation of at least one *Monascus* species. These compositions are useful for prevention and treatment of osteoporosis in mammals, and in particular humans. The methods of the present invention are based, in part, on the discovery that the fermentates of *Monascus* species display such properties. The ability of red rice products to prevent or treat osteoporosis provides the art with a unique, natural alternative to the use of prescription compounds.

According to the invention, traditional or improved red rice can be prepared by traditional fermentation procedures or by modification of the traditional procedures. According to the earliest reported method (Sung, 1637, T'ien Kung K'ai Wu; pages 291-294, English translation by Sun et al., Pennsylvania State Press 1966), red rice can be prepared by the fermentation of washed and cooked nonglutinous rice using red wine mash, natural juice of Polygonum grass, and alum water. The rice is fermented in open air for 7 days on bamboo trays under very clean conditions. The rice changes its color from white to black, black to brown, brown to red and then red to yellow, which is then harvested as red rice. According to an alternative traditional method, nonglutinous rice can be fermented in a hole in the ground lined by bamboo mats, which is securely covered. Fermentation is allowed to take place underground for one year or more, up to four years.

With respect to the present invention, the traditional method has been improved by use of modern fermentation techniques and equipment to more precisely control the temperature, pH, pressure and other fermentation parameters, which, inter alia, reduce the time of fermentation. The preparations can be made as follows:

Preparation of Conventional Culture Fluid

For all of the media preparations rice or another grain is used as a carbon source. The carbon source can be rice (polished long-grain nonglutinous rice, polished round-grain nonglutinous rice, polished glutinous rice, red rice, and black rice), millet, barley, wheat, or corn. Additional sugar and substances containing sugar can be used. Organic compounds such as glycerine and glyceride can also be used in the media preparations. For each 100 g of polished round-grained nonglutinous rice, 30-80 ml of culture medium are added. The culture media's key feature is that the carbon source is selected from the group consisting of cereals, sugar, and organic compounds; the source of nitrogen is selected from the group consisting of beans (e.g., soya bean powder, pressed soybean cake), or peanut powder (or pressed peanut cake), peptone, rice extract powder, thick beef juice, silkworm chrysalis powder, or inorganic salts (e.g., $NH_4NO_3$, etc.); and a source of phosphorous can also be added, such as inorganic salts (e.g., $KH_2PO_4$, $K_2HPO_4$, etc). Other inorganic salts can also be added, such as $MgSO_4$ or $FeCl_2$. By way of an example, and not by limitation, media preparations of the invention are listed below:

Media 1: Liquid strain
2-7% glycerine (or malt or potato juice)
2-6% sugar
0-3% peptone
0.5-3% yeast extract powder
0-3% thick beefjuice (optional)
2-4% defoamer (e.g., bean oil or peanut oil)
water Media 2: Solid strain
0-5% potato juice
0-6% sugar
0-1.5% yeast extract or peptone
30-80 ml of water per 100 g rice Media 3:
2-4% potato juice
2-6% sugar
0.5-3% yeast extract powder (or peptone or thick beef juice)
water.

Approximately 40-80 ml of the mixture is added to each 100 g of rice, the pH is maintained at 3-8, and it is sterilized in steam at 121° C.

Generally, the pH is adjusted to 3.0-5.0, and the mixture is steam sterilized (121° C.). The mixture is cooled to 40° C., and the rice is inoculated with a *Monascus* strain of the invention. For example, the *Monascus purpureus* Went strain CGMCC No. 0272 is added and cultured at 15-35° C. for 9 days. Fermentation of the rice mixture is preferably carried out at a temperature of 15-35° C., most preferably 20-28° C., and a period of over 4 days, most preferably 9 days or more, until the formation of red rice is noted. Any one of a number of methods of fermentation, well known to one of skill in the art, can be used. For example, an Erlenmeyer flask, tray, or ventilated fermentation bed can be used as fermentation facilities. At the end of the fermentation process, the fermentation broth is drained and discarded, while the solid residue is sterilized by heat (for example, by high pressure steam). For example, the fermentation product is sterilized at a temperature of 69-121° C. and dried. This dried product can be ground. Standard mesh sizes for the production of capsules, tablets, powders and suspensions are well known in the art. By way of example, the improved red rice of the invention can be ground to 80 mesh under vacuum at a temperature of approximately 60-80° C., and the powdered product recovered. This product can be used directly in the various compositions and formulations provided by the present invention. For example, it can be filled into capsules. The capsules used in tests described below labeled as P3 are 300 mg capsules containing 20 mg/g lovastatin. Alternatively, the 80 mesh ground product can further be ground to 200 mesh. The 200 mesh powder can then be formulated into tablets using standard methodologies. Alternatively, liquid or syrup formulations of red rice can be made using conventional procedures.

Optionally, the dried crushed red rice powder can be further processed, e.g., extracted with organic solvents, such as but not limited to, alcohols (e.g., 75-90% ethanol), to remove starch and/or agar. After evaporation to dryness, the extract can be used in the various compositions and formulations as provided by the present invention. The extracted product can further be concentrated under a vacuum and evaporated (60-80° C., 0.06-0.08 MPa) until dry. This provides an exceptionally useful supplement at very low cost.

According to the invention, an "improved red rice" is produced by fermentation using one or more natural or mutant strains of *Monascus* species, which yield a fermentate with improved biological or nutritional properties, e.g., higher hypocholesterolemic and hypotriglyceridemic activities than traditional red rice. The improved red rice of the invention comprises *Monascus purpureus* Went mutant strain M4027, 4028 and M4184. Several other strains can be used to achieve the objectives of the invention (*Chinese Microorganism Strain Index,* 1992, China Microorganism Collection Committee), as listed in the Table above.

Lovastatin in red rice may be extracted using 10 ml of 75% EtOH at ambient temperature. The extract (2 ml) is treated with 1 ml 0.06 M NaOH in 75% EtOH for 30 min, then with 1 ml 0.06 N $H_3PO_4$ (in 75% EtOH), and the mixture applied to a C18 HPLC column (150×4.60 mm), and developed with 0.02 N $H_3PO_4$ (in 70% MeOH) to quantify the amount of lovastatin present.

The present invention encompasses a composition comprising a therapeutically effective amount of a red rice product, for example 2-4 grams per day, useful in humans for the treatment or prevention of osteoporosis.

Lovastatin-hydroxy acid

Lovastatin-lactone

Functions of Improved Red Rice

The improved red rice of the invention and preparations of the improved red rice contain statinoid compounds, i.e., hydroxy-acid lovastatin and lactone lovastatin.

Method of Treatment

The present invention provides methods for treating a human afflicted by osteoporosis. In addition to treatment of a human disease, the methods of the invention can also be used for preventive treatment in a person susceptible to such disease.

As used herein, examples of osteoporosis may include primary osteoporosis and secondary osteoporosis.

The preventive or therapeutic dose of traditional red rice or improved red rice in the treatment or prevention of osteoporosis and the management of bone density will vary with the condition to be treated and the severity of the condition to be treated. The dose, and perhaps the dose frequency, will also vary according to the age, body weight, and response of the individual patient. In general, the total daily dose range of red rice, for the conditions described herein, is from about 0.1 g to about 5 g administered in single or divided doses orally. For example, a preferred oral daily dose range should be from about 0.3 g to about 4 g, while most preferably an oral daily dose should be about 1.2 to about 2.5 g. For example, two capsules each containing 0.6 g of red rice may be taken orally twice a day to obtain the preferred dosage. A course of treatment should be at least 12 weeks. It may be necessary to use dosages outside these ranges in some cases as will be apparent to those skilled in the art. Further, it is noted that the nutritionist, dietitian, clinician or treating physician will know how and when to interrupt, adjust, or terminate therapy according to the response of individual patients.

It should be noted that the present invention encompasses new uses of traditional red rice, and novel red rice products and novel methods of using those products.

Dietary Supplement Use

As mentioned above, the present invention encompasses compositions and methods of using traditional, novel or improved red rice products as dietary supplements. As such, the red rice products provide the individual with a means for maintaining normal or healthy bone mass despite intrinsic deterioration, e.g., from aging, menopause or extrinsic factors such as poor nutrition. The dietary supplements also provide means for preventing, or reducing the likelihood of experiencing, the diseases discussed above. The dietary supplements containing red rice products are particularly useful for the elderly and postmenopausal women. The dietary supplements should be taken daily for at least twelve weeks and can be used permanently on a daily basis. A daily dose is from about 0.1 g to about 5.0 g; preferably about 1 to about 4 g; and most preferably about 1.2 to about 2.4 grams per day.

Formulation

The pharmaceutical and dietary compositions of the present invention comprise a red rice product, or an extract thereof, as active ingredient, and may also contain a pharmaceutically acceptable carrier or excipient and, optionally, other ingredients.

Other ingredients that can be incorporated into the dietary or pharmaceutical compositions of the present invention may include, but are not limited to, vitamins, amino acids, metal salts and flavor enhancers. For oral administration, the compositions comprising red rice can be added directly to food so that a therapeutically effective amount of red rice is ingested during normal meals. Any methods known to those skilled in the art may be used to add or incorporate red rice to natural or processed food.

Compositions of the present invention suitable for oral administration may be presented as discrete units such as capsules, cachets, or tablets, each containing a predetermined amount of a red rice product, as a powder or granules, or as a solution or a suspension in an aqueous liquid, a nonaqueous liquid, an oil-in-water emulsion, or a water-in-oil liquid emulsion. In general, the compositions are prepared by uniformly and intimately admixing the active ingredient with liquid carriers or finely divided solid carriers or both, and then, if necessary, shaping the product into the desired presentation.

The compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Liquid preparations for oral administration can take the form of, for example, solutions, syrups or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats), emulsifying agents (e.g., lecithin or acacia), nonaqueous vehicles (e.g., almond oil, oily esters, ethyl alcohol or fractionated vegetable oils), and preservatives (e.g., methyl or propyl-p-hydroxybenzoates or sorbic acid). The preparations can also be made to resemble food, containing buffer salts, flavoring, coloring and sweetening agents as appropriate.

Any dosage form may be employed for providing the patient with an effective dosage of the red rice product. Dosage forms include tablets, capsules, dispersions, suspensions, solutions, capsules and the like. Because of their ease of administration, tablets and capsules represent the most advantageous oral dosage unit form, in which case solid pharmaceutical carriers as described above are employed. In addition to the common dosage forms set out above, the compounds of the present invention may also be administered by controlled release means. However, the most preferred oral solid preparations are capsules.

For example, a tablet may be prepared by compression or molding, optionally with one more accessory ingredients. Compressed tablets may be prepared by compressing in a suitable machine red rice in a free-flowing form such as powder or granules, optionally mixed with a binder, lubricant, inert diluent, surface active or dispersing agent. Most preferably, the composition is a capsule containing 0.3 g of red rice in powder form.

The invention is further defined in the following examples and experiments conducted to study the efficacy and safety of red rice. It will be apparent to those skilled in the art that many modifications, both to materials and methods, may be practiced which are within the scope of this invention.

The invention will be further described in the following examples, which are intended to provide further description of the invention, and are not intended to limit the scope of the claims.

EXAMPLE 1—PREPARATION OF RED RICE CULTURES (A) A liquid strain culture fluid was prepared containing 2-4% glucose, 3-5% glycerine, 0-3% thick beefjuice, 0.8-1.6% peptone, 0-3% yeast extract powder, 0.1% $KH_2PO_4$, and 0.05% $MgSO_4.7H_2O$ and water. Two media were prepared, the first containing 2% glucose, 3% glycerine, 1.5% thick beef juice, 0.8% peptone, 3% yeast extract powder, 0.1% $KH_2PO_4$, and 0.05% $MgSO_4.7H_2O$ in water, and the second containing 4% malt juice or potato juice, 8% sugar, 1.5% yeast extract powder, 3% thick beef juice, and water. The pH was adjusted to 3.5 using acetic acid. For each 50 ml of culture fluid, 100 g of polished round-grained nonglutinous rice was added, and the media were sterilized in steam at 121° C. The mixture was cooled to below 40° C. inoculated with *Monascus purpureus* Went (CGMCC No. 0272) in glass tubes or plates, and cultured at 30-34° C. for 24-36 hours. Fermentation was continued at 25° C. for 9 days. Once the fermentation period was completed, the mixture was sterilized at high temperature (100-121° C.), dried under a vacuum at 80° C., and ground to 60-100 mesh. The powder was then filled into capsules. The yield was approximately 65%.

(B) Alternatively, culture fluid containing 4% malt juice or potato juice, 8% glucose, 3% thick beef juice, 3% peptone and water (pH value adjusted to 3) was used. Following fermentation, the resulting product was extracted using 75-95% ethanol, the red rice was dried and fully mixed with untreated rice. Soya bean powder (10 g) and culture fluid (50 ml) were added to each 100 g mixture, and the composition was sterilized. The mixture was cooled to 30-40° C. and then inoculated with 10-20 ml liquid *Monascus* strain (CGMCC No. 0272), fermented at 30-34° C. for 3-4 days and at 23-25° C. for over 15 days. The mixture was sterilized at 100-121°

C. and dried under vacuum. This red rice product was ground and tablets were produced.

(C) Another medium was prepared using 4% malt juice, 6% malt sugar, 1% yeast extract powder, 6% peptone and water (pH=3). Soya bean powder (15 g) and culture fluid (50 ml) was added to each 100 g of polished round-grained nonglutinous rice. The mixture was sterilized at 121° C. and then inoculated with *Monascus ruber* AS 3.549 (20 ml). Fermentation was carried out at 25° C. for over 9 days. After sterilization, the mixture was dried at 80° C.

The red rice was further processed into concentrates using alcohol (75%) extraction twice. After evaporation under vacuum, the concentrated substance was obtained and the alcohol was recovered. The resulting concentrated substance contained approximately 25 mg lovastatin per gram red rice, and was used as raw material for the production of the capsules or tablets.

(D) Another culture fluid was prepared containing 4% malt juice, approximately 8% sugar, 2% yeast extract powder, 5% thick beef juice and water (pH=3). Culture fluid (50 ml) was added to each 100 g of rice and the mixture was sterilized in steam at 121° C. After cooling below 40° C., the mixture was inoculated with *Monascus albidus* (CGMCC No. 0317) and then fermented at 25° C. for over 12 days. The mixture was sterilized and then dried. This red rice preparation was ground to 200 mesh and granulated with alcohol for pill preparation.

(E) Culture fluid was also prepared using 3% potato juice, approximately 6% sugar, 1.5% yeast extract powder, 4% peptone and water (pH=3). Soya bean powder (10 g) and culture fluid (80 ml) were added to each 100 g of rice and the mixture was sterilized in steam at 121° C. After cooling below 40° C., the mixture was inoculated with *Monascus pilosus* Sato (AS 3.4444), cultured at 30-34° C. for 3-4 days, then cultured for over 10 days at 100-121° C. and dried.

This red rice preparation was further processed into concentrates by using alcohol (75%) extraction. Small amounts of dissolvable starch were added for pill preparation.

(F) Culture fluid was also prepared using 3% potato juice, 5% sugar, 6% thick beef juice and water (pH=3). 10-20% peanut powder was added to culture fluid (80 ml) for each 100 g of rice, and the mixture was sterilized in steam at 121° C. After cooling below 40° C., the mixture was inoculated with *Monascus ruber* van Tieghem (CGMCC No. 0315) and then cultured at 30-34° C. for 3 days. The temperature was lowered to 24° C. and the culturing was continued for over 15 days. The mixture was sterilized in steam at 100-121° C. and dried.

(G) A medium was also prepared containing 3% corn juice or 3% potato juice, 6% sugar, 1.5% yeast extract powder, 4.5% peptone and water (pH=3). 5-20% of soya bean cake powder and 80 ml of culture fluid were added to each 100 g of millet. The mixture was sterilized in steam at 121° C., cooled to a temperature below 40° C., inoculated with *Monascus pilosus* (AS 3.4633), and cultured at 25° C. for over 18 days. The mixture was sterilized at 121° C. and then dried under a vacuum at a temperature of 60-80° C.

(H) A medium was prepared containing 4% potato juice, 7% sugar, 8% peptone and water (pH=3). Culture fluid (60 ml) was added to each 100 g of rice, and the mixture was sterilized at 121° C. After cooling to a temperature below 40° C., the mixture was inoculated with *Monascus pubigerus* Sato (AS 3.4445), and then cultured at 30-34° C. for 3 days. The temperature was lowered to 25° C. and culturing was continued for over 9 days. The mixture was sterilized in steam at 121° C. and dried at 80° C.

(I) A medium was prepared containing 5% soya bean milk, 5% glucose, 2% yeast extract powder, 5% soya bean peptone and water (pH=3). Culture fluid (80 ml) was added to each 100 g of rice and the mixture was sterilized in steam at 121° C. After cooling to a temperature below 40° C., the mixture was inoculated with *Monascus pilosus* Sato (AS 3.4646), and cultured at 30-34° C. for 3 days. The temperature was lowered to 23-25° C., and cultured for over 9 days. The mixture was sterilized in steam at 121° C. and then dried at 80° C.

(J) A medium was prepared containing 4% potato juice, 4% sugar, 3% yeast extract powder and water (pH=3). Silkworm chrysalis powder (5 g) and culture fluid (60 ml) were added to each 100 g of rice, and the mixture was sterilized in steam at 121° C. After cooling to a temperature below 40° C., the mixture was inoculated with *Monascus fuliginosus* Sato (AS 3.569), and then cultured at 30-34° C. for 3 days. The temperature was lowered to 23-25° C. and culturing was continued for over 9 days. The mixture was sterilized in steam at 121° C. and dried under vacuum at 60-80° C.

(K) A medium was prepared containing 3% malt juice, 5% sugar, 6% thick beef juice and water (pH=3). Culture fluid (80 ml) was added to each 100 g of rice, and the mixture was sterilized in steam at 121° C. After cooling to a temperature below 40° C., the mixture was inoculated with *Monascus fuliginosus* Sato (AS 3.1098), and then cultured at 30-34° C. for 3 days. The temperature was lowered to 23-25° C. and culturing continued for over 9 days. The mixture was sterilized in steam at 121° C. and dried at a temperature of 80° C.

(L) The following procedures were used for large-scale fermentation:

(1) Soaking the rice: Rice (500 kg) was placed in several layers of baskets. The chaff was cleaned in water, and the rice soaked in water for 16-24 hours. The rice was dredged from the water and dried (the content of water is approximately 22-24%).

(2) Steaming the rice: Dried rice was poured into a rice steamer and steamed for 50-70 minutes. The steamed rice was spread out on a bamboo mat or in baskets, dispersed, and cooled to a temperature below 40° C. The rice was then inoculated with approximately 20 kg of solid *Monascus* strain and 2.5-3 kg of acetic acid and stirred.

(3) Fermentation: For the first 3 days, the rice was turned over several times per day. The temperature was controlled between 30° C. and 34° C. After 3 days, the temperature was reduced to 23-25° C. The rice was turned over once daily, during which water (pH value adjusted to 3.5 using acetic acid) was added at quantity depending on the humidity of the fermenting mixture. The mixture was fermented for over 15 days.

(4) Preservation: After the fermentation process, the mixture was sterilized, dried and preserved.

The large-scale fermentation methods were used with all media and preparative processes described above by adding in the respective proportions of other ingredients. It should be noted that forced ventilation can be used in the fermentation process but that the return air must be sterile.

EXAMPLE 2—INDUCING OSTEOPOROSIS IN OOPHORECTOMIZED RATS

Fifty-eight female Wistar rats were selected, all of the Clean Grade and each weighing 174 g-197 g. The rats were supplied by the Experiment Animals Institute of the Chinese Academy of Medical Sciences.

The 58 rats were randomly divided into 5 groups, namely:

| I. | Normal Group (ovaries intact) | 6 rats |
| II. | Control Group (untreated oophorectomized) | 11 rats |
| III. | P3 Low Dosage Group | 15 rats |
| IV. | P3 Medium Dosage Group | 15 rats |
| V. | P3 High Dosage Group | 11 rats |

The P3 capsules were prepared as described above, and dosages were adjusted by animal weight.

Control Group: Anesthetizing a rat by an abdominal injection of pentobarbital at 45 mg/kg of the body weight; placing the rat at an abdominal posture; cutting the hair below the last rib, near the intersection of the midaxillary line and the spine, approximately 1 cm off the outer side of the spine; administering disinfection with 70% alcohol and iodine tincture; cutting through the skin, the dorsal muscle, and the peritoneum; using forceps to pull the white mass of fat out of the incision; separating the mass of fat to reveal the ovary; performing the ligation of the lower end of the fallopian tube with silk ligature; removing the ovary; stitching the incision and applying antiphlogistics on the surface; and, then, repeating the procedure to remove the other ovary.

Three months after the oophorectomy, the rats in the three Dosage Groups were given—continuously for three months—Low Dosage P3 Capsules, Medium Dosage P3 Capsules, and High Dosage P3 Capsules, respectively. Eighteen days and eight days before being put to death, the rats received abdominal injections of tetracycline hydrochloride at 30 mg/kg of the body weight respectively for the fluorescent marking of the bones. After receiving the P3 Capsules for three months, the rats were put to death. Their tibias were collected for non-decalcified bone section tests.

Staining of Non-Decalcified Bone Sections

The preparation procedure was as follows: obtaining the near-end ⅓ length of a rat's left tibia; removing the soft tissue; and performing multiple-stage dehydration by ethyl alcohol and hyalinization by xylene, with the process being conducted twice at each stage—each time lasting for 24 hours. The immersion solutions were prepared in the following manner: Solution I: methylmethacrylate 75 ml and dibutyl phthalate 25 ml; Solution II: adding benzoyl peroxide 1 g to Solution I; Solution III: adding benzoyl peroxide 2.5 g to Solution I. The three Solutions were thoroughly mixed in magnetic stirrers, respectively. The samples were immersed in Solutions I, II, and III for 36 hours. Approximately 5 ml of Solution III was injected into a penicillin ampoule and, then, the samples—arranged in the same direction—were placed into the ampoule. The ampoule was then placed in an oven for the samples to go through polymerization at 40° C. for 3-4 days. After the samples were transformed into a colorless, transparent, and hard embedded block, the ampoule was taken out of the oven and broken open to yield the embedded block. After the block was trimmed, a Reicheit-June 2040 cutting machine with tungsten steel blades was employed to cut the block into longitudinal non-decalcified bone sections of 5 μm and 10 μm in thickness. The 5 μm slices were placed in a xylene solution to remove the resin ingredients and then were subjected to gradient elution from ethyl alcohol to water. The 5 μm slices were to be used for toluidine staining. The 10 μm slices were to be used in fluorescent tests.

EXAMPLE 3—DETERMINATION OF THE MEASUREMENT INDICATORS IN BONE STRUCTURE MORPHOLOGY

This study followed the procedures adopted by Zhang Mingfang et al, Chinese J. Osteopathy, 1994, 14(b): 365, in taking the bone structure morphological measurements with a Leica Owin graphic analysis system.

Measuring the Bony Trabecula Structure Morphology

Bony Trabecula Volume Percentage (TBV %): Measurement of the bony trabecula volume as a percentage of the total medullary volume to be measured. This value was a major indicator in the quantitative study of the bone structure morphology.

Bony Trabecula Resorption Surface Percentage (TRS %): Measurement of the irregular and uneven bony trabecula surface as a percentage of the total bony trabecula surface.

Bony Trabecula Formation Surface Percentage (TFS %): Measurement of the osteoid surface covered with osteoblasts as a percentage of the total bony trabecula surface.

Active Formation Surface Percentage (AFS %): Measurement of the bony trabecula surface with fluorescent marking stripes as a percentage of the total bony trabecula surface.

Bony Trabecula Mineralization Rate (MAR): Quotient of the average distance between the two fluorescent marking stripes on the bony trabecula surface divided by the number of days of the interval between the first marking date and the second marking date.

Measuring the Cortical Inner Surface Morphology

Average Osteoid Width (OSW): Average width of the osteoid on the cortical inner surface.

Osteo Cortex Mineralization Rate (mAR): Quotient of the average distance between the two fluorescent marking stripes on the cortical inner surface divided by the number of days of the interval between the first marking date and the second marking date.

Statistical Handling

The measurements obtained were all represented as the Average Value+the Standard Deviation and verified by Student's t test.

Results

1. Effect of the P3 Capsules on the Tibia TBV % Values in Oophorectomized Rats

In comparison with the Normal Group, the tibia TBV % values of the Control Group, the P3 Low Dosage Group, the P3 Medium Dosage Group, and the P3 High Dosage Group substantially decreased. In comparison with the Control Group, the tibia TBV % value of the P3 High Dosage Group substantially increased, that of the P3 Medium Dosage Group somewhat—not substantially—increased, and that of the P3 Low Dosage Group did not show any substantial change. See Table 1.

TABLE 1

Changes in Tibia TBV % Values among the Groups

| Groups | N | TBV % |
|---|---|---|
| Normal Group | 6 | 31.77 ± 3.87 |
| Control Group | 11 | 13.91 ± 4.83** |
| P3 Low Dosage Group | 15 | 15.16 ± 5.03** |

TABLE 1-continued

Changes in Tibia TBV % Values among the Groups

| Groups | N | TBV % |
|---|---|---|
| P3 Medium Dosage Group | 15 | 17.20 ± 4.47** |
| P3 High Dosage Group | 11 | 22.52 ± 6.42** ΔΔ |

Notes:
In comparison with the Normal Group: **P < 0.01.
In comparison with the Control Group: ΔΔP < 0.01.

2. Effect of the P3 Capsules on the Tibia TRS % Values in Oophorectomized Rats

In comparison with the Normal Group, the tibia TRS % values of the Control Group, the P3 Low Dosage Group, the P3 Medium Dosage Group, and the P3 High Dosage Group substantially increased. In comparison with the Control Group, the tibia TBV % values of the P3 Medium Dosage Group and the P3 High Dosage Group substantially decreased, and that of the P3 Low Dosage Group did not show any substantial change. See Table 2.

TABLE 2

Changes in Tibia TRS % Values among the Groups

| Groups | n | TRS % |
|---|---|---|
| Normal Group | 6 | 2.63 ± 0.51 |
| Control Group | 11 | 12.64 ± 4.66** |
| P3 Low Dosage Group | 15 | 10.51 ± 3.04** |
| P3 Medium Dosage Group | 15 | 8.35 ± 1.76** ΔΔ |
| P3 High Dosage Group | 11 | 4.99 ± 1.76** ΔΔ |

Notes:
In comparison with the Normal Group: **P < 0.01.
In comparison with the Control Group: ΔΔP < 0.01.

3. Effect of the P3 Capsules on the Tibia TFS %, AFS %, and MAR Values in Oophorectomized Rats In comparison with the Normal Group, the tibia TFS %, AFS %, and MAR values of the Control Group, the P3 Low Dosage Group, the P3 Medium Dosage Group, and the P3 High Dosage Group substantially increased. In comparison with the Control Group, the TFS %, AFS %, and MAR values of the P3 High Dosage Group substantially decreased; the TFS % and AFS % values of the P3 Medium Dosage Group substantially decreased, but its MAR value did not show any substantial change; and the TFS %, AFS %, and MAR values of the P3 Low Dosage Group did not show any substantial change. See Tables 3 and 4.

TABLE 3

Changes in Tibia TFS % Values among the Groups

| Groups | n | TFS % |
|---|---|---|
| Normal Group | 6 | 2.94 ± 0.76 |
| Control Group | 11 | 11.85 ± 4.25** |
| P3 Low Dosage Group | 15 | 11.23 ± 4.20** |
| P3 Medium Dosage Group | 15 | 8.48 ± 2.29** Δ |
| P3 High Dosage Group | 11 | 5.27 ± 2.14* ΔΔ |

Notes:
In comparison with the Normal Group: *P < 0.05; **P < 0.01.
In comparison with the Control Group: ΔP < 0.05; ΔΔP < 0.01.

TABLE 4

Changes in Tibia AFS % and MAR Values Among the Groups

| Groups | n | AFS % | MAR (μm/d) |
|---|---|---|---|
| Normal Group | 6 | 6.19 ± 0.92 | 0.83 ± 0.06 |
| Control Group | 11 | 32.76 ± 15.13** | 1.69 ± 0.28** |
| P3 Low Dosage Group | 15 | 28.57 ± 9.89** | 1.61 ± 0.20** |
| P3 Medium Dosage Group | 15 | 23.47 ± 4.85** Δ | 1.49 ± 0.28** |
| P3 High Dosage Group | 11 | 14.25 ± 5.67** ΔΔ | 1.21 ± 0.15** ΔΔ |

Notes:
In comparison with the Normal Group: **P < 0.01.
In comparison with the Control Group: ΔP < 0.05; ΔΔP < 0.01.

4. Effect of the P3 Capsules on the Tibia OSW and mAR Values in Oophorectomized Rats In comparison with the Normal Group, the tibia OSW and mAR values of the Control Group, the P3 Low Dosage Group, the P3 Medium Dosage Group, and the P3 High Dosage Group substantially increased. In comparison with the Control Group, the OSW and mAR values of the P3 High Dosage Group showed a decrease, but of no statistical significance; and the OSW and mAR values of the P3 Medium Dosage Group and the P3 Low Dosage Group did not show any substantial change. See Table 5.

TABLE 5

Changes in Tibia OSW and mAR Values among the Groups

| Groups | n | OSW | mAR (μm/d) |
|---|---|---|---|
| Normal Group | 6 | 11.39 ± 2.29 | 1.55 ± 0.13 |
| Control Group | 11 | 15.05 ± 1.39** | 2.48 ± 0.36** |
| P3 Low Dosage Group | 15 | 15.23 ± 1.42** | 2.47 ± 0.15** |
| P3 Medium Dosage Group | 15 | 13.89 ± 1.97* | 2.45 ± 0.21** |
| P3 High Dosage Group | 11 | 13.74 ± 1.69* | 2.12 ± 0.59* |

Note:
In comparison with the Normal Group: *P < 0.05; **P < 0.01.

This quantitative study of the bone structure morphology revealed that the tibia TBV % value, which was regarded as a major indicator, of the oophorectomized rats substantially decreased while the TRS % value (an indicative bone resorption parameter), the TFS % value (an indicative bone formation parameter), and the AFS %, MAR, OSW and mAR values substantially increased. This was an indication that the osteoporosis caused by oophorectomy was a high conversion type, wherein the bone resorption rate was greater than the bone formation rate. The administration of the P3 Capsules to the oophorectomized rats brought about the following results: in the P3 High Dosage Group, the trends of changes mentioned above were reversed; in other words, the TBV % value substantially increased while the TRS %, TFS %, AFS %, and MAR values substantially decreased, and the OSW and mAR values also moved lower; in the P3 Medium Dosage Group, the TBV % value moved lower while the TRS %, TFS % and AFS % values substantially decreased; and in the P3 Low Dosage Group, the parameters did not show any substantial change. The pharmacodynamic results indicated that high-dosage P3 Capsules had some therapeutic effect on osteoporosis caused by oophorectomy, that medium-dosage P3 Capsules might have some therapeutic effect, and that low-dosage P3 Capsules did not have therapeutic effect.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of treating or osteoporosis in a mammal suffering from osteoporosis, said method comprising:
   administering to the mammal an effective amount of a red rice fermentation product produced from the fermentation of at least one lovastatin-producing *Monascus* strain, wherein the osteoporosis is a primary osteoporosis or a secondary osteoporosis induced by a disease.

2. The method of claim 1, wherein said osteoporosis is a primary osteoporosis.

3. The method of claim 1 or 2, wherein said *Monascus* strain comprises a strain selected from the group consisting of *Monascus albidus* Sato AS 3.570, AS 3.4440, CGMCC No. 0317; *Monascus pilosus* Sato AS 3.4444, AS 3.4633, AS 3.4646, AS 3.4647; *Monascus pubigerus* Sato AS 3.4445; *Monascus ruber* van Tieghem AS 3.549, CGMCC No. 0315, CGMCC No. 0316; *Monascus paxii* Lingelsheim AS 3.4453; *Monascus fuliginosus* Sato AS 3.569, AS 3.1098, AS 3.2091, AS 3.2093, AS 3.2134, IFFI 05035, and *Monascus purpureus* Went CGMCC No. 0272.

* * * * *